US005521237A

United States Patent [19]

Seltzer et al.

[11] Patent Number: 5,521,237
[45] Date of Patent: May 28, 1996

[54] ALKANOLAMINE ESTERS OF ACYCLIC PHOSPHITES IN POLYOLEFIN COMPOSITIONS

[75] Inventors: Raymond Seltzer, New City, N.Y.; Wha Chen, Mobile, Ala.; Roswell E. King, III, Pleasantville, N.Y.; Paul Odorisio, Leonia, N.J.; Rita Pitteloud, Praroman, Switzerland; Sai P. Shum, Pleasantville, N.Y.

[73] Assignee: Ciba-Geigy Corporation, Tarrytown, N.Y.

[21] Appl. No.: 254,203

[22] Filed: Jun. 6, 1994

[51] Int. Cl.$^6$ .................................................. C08K 5/526
[52] U.S. Cl. ........................... 524/128; 524/148; 554/4; 558/158; 558/166; 252/49.9
[58] Field of Search ............................. 524/128, 148; 558/158, 166

[56] References Cited

PUBLICATIONS

Chem. Abstr. 121:147703; Gavrilov, K. N. et al., Zh. Obshch. Khim. 1993, 63(12), 2791–2802.
Chem. Abstr. 109:129162; Pastor, S. D. et al., J. Am. Chem. Soc. 1988, 110(19), 6547–6555.
Chem. Abstr. 97:163115; Pudovik, M. A. et al., Zh. Obschch. Khim. 1982, 52(7), 1481–1487.

Primary Examiner—Johann Richter
Assistant Examiner—Michael G. Ambrose
Attorney, Agent, or Firm—Luther A. R. Hall

[57] ABSTRACT

Selected alkanolamine esters of acyclic phosphites are particularly effective as process stabilizers for polyolefins providing for melt flow stabilization and resistance to discoloration during said processing.

10 Claims, No Drawings

ALKANOLAMINE ESTERS OF ACYCLIC PHOSPHITES IN POLYOLEFIN COMPOSITIONS

This invention pertains to selected novel alkanolamine esters of acyclic phosphites which are particularly effective as process stabilizers for polyolefins providing for melt flow stabilization and resistance to discoloration during said processing.

BACKGROUND OF THE INVENTION

Organic phosphites have long been known as process stabilizers. The exact chemical structure of the phosphite, however, is important in determining the particular efficacy of said phosphite as a process stabilizer.

The compounds and compositions of this invention are structurally distinct from the prior art compounds and compositions of U.S. Pat. Nos. 4,318,845; 4,374,219; 4,524,166; and 2,841,607; and EP 511,156 A2. In addition, the instant compounds and compositions of this invention offer the following advantages over the prior art compounds and compositions:

(1) Superior polymer stabilizing properties during high temperature processing;

(2) Low color development and color maintenance during processing especially when used in combination with phenolic antioxidants;

(3) Superior storage stability particularly hydrolytic stability;

(4) Better compatibility with and ease of incorporation into the substrate to be stabilized;

(5) Superior physical forms which provide advantages in handling, transporting, and blending; and (6) More effective incorporation in spray on applications resulting in superior in polymer performance.

OBJECTS OF THE INVENTION

The objects of this invention are:

(1) Novel alkanolamine esters of acyclic phosphites;

(2) Stabilized polyolefin compositions containing novel alkanolamine esters of acyclic phosphites that provide melt flow stabilization and color retention during processing; and (3) Stabilized polyolefin compositions containing novel alkanolamine esters of acyclic phosphites in combination with a hindered phenolic antioxidant and/or a hindered amine stabilizer and/or a hydroxylamine and/or a benzofuran-2-one.

DETAILED DISCLOSURE

More particularly, the instant invention pertains to alkanolamine esters of acyclic phosphites of formula I

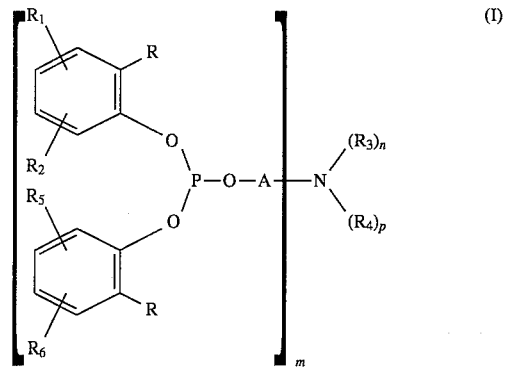

such that when:

m is 1, then n is 1 and p is 1;
m is 2, then n is 1 and p is 0;
m is 3, then n is 0 and p is 0;

wherein

A is alkylene of 2 to 8 carbon atoms or cycloalkylene of 5 to 6 carbon atoms;

$R, R_1, R_2, R_5$ and $R_6$ are independently hydrogen or alkyl of 1 to 18 carbon atoms or phenyl;

$R_3$ is hydrogen, alkyl of 1 to 18 carbon atoms, phenyl or a group of the formula

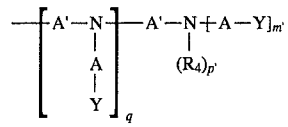

wherein Y is a group of the formula

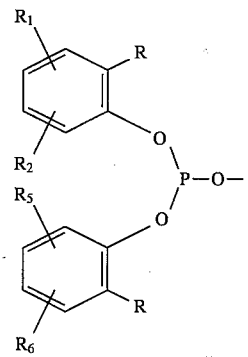

A' is alkylene of 2 to 8 carbon atoms or cycloalkylene of 5 to 6 carbon atoms, when m' is 1, then p' is 1,
when m' is 2, then p' is 0, and q is 0–5 with A, R, $R_1$, $R_2$, $R_5$ and $R_6$ being as previously defined, with the proviso that, when p and q are 0, then —N—A'—N— can be a diazacycloalkylene group of 4 to 10 carbon atoms; or when m is 1 and p is 0, then N—$R_3$ is an azacycloalkyl group of 4 to 10 carbon atoms or an azaoxacycloalkyl group of 4 to 7 carbon atoms; and $R_4$ is hydrogen, alkyl of 1 to 18 carbon atoms or phenyl; and with the further proviso that when R is tert-butyl, $R_1$ and $R_5$ are 4-tert-butyl, and $R_2$ and $R_6$ are 6-methyl, then m is 3.

This latter proviso denotes a selection from within the teachings of EP 511,156 A2.

Preferably, the instant compounds are those where in formula I, R is alkyl of 2 to 8 carbon atoms, and $R_1$ and $R_5$ are alkyl of 1 to 8 carbon atoms, and $R_1$ and $R_5$ are in the ortho or para position to the phosphite oxygen in each of the phenyl rings.

Also preferred are compounds of formula I wherein m is 3, and n and p are 0.

Most preferably, the instant compounds of formula I are those where

R is iso-propyl, sec-butyl, tert-butyl, tert-amyl or tert-octyl group, $R_1$ and $R_5$ are alkyl of 1 to 8 carbons, and $R_1$ and $R_5$ are in the ortho or para position to the phosphite oxygen in each of the phenyl rings; and m is 3, and n and p are 0.

The instant invention also pertains to a composition stabilized against thermal, oxidative and actinic induced degradation which comprises (a) an organic material subject to thermal, oxidative or actinic induced degradation, and (b) an effective stabilizing amount of an alkanolamine ester of formula I as defined above.

The compounds of the instant invention are prepared by reacting an appropriate alkanolamine with a substituted chlorophosphite (or phosphorochloridite) in the presence of an acid acceptor as seen in Example 1. The intermediate chlorophosphites are prepared by reaction of a substituted phenol with phosphorus trichloride as seen in Example 4. These intermediates are generally items of commerce or can be prepared by known methods.

When any of R or $R_1$ to $R_4$, is alkyl, such alkyl groups are, for example, methyl, ethyl, isopropyl, n-butyl, tert-butyl, tert-amyl, 2-ethylhexyl, n-octyl, n-undecyl, lauryl, n-heptadecyl and n-octadecyl; when A or A' is alkylene, such alkylene groups are, for example, ethylene, trimethylene, tetramethylene, hexamethylene, octamethylene and 2,2-dimethylpropane-1,3-diyl; when A or A' is cycloalkylene, such cycloalkylene groups are, for example, cyclopentylene or cyclohexylene; when —N—A'—N— is a diazacycloalkylene group, —N—A'—N— is, for example, piperazin-1,4-diyl or homopiperazin-1,4-diyl; and when —N—$R_3$ is azacycloalkyl or azaoxacycloalkyl, —N—$R_3$ is, for example, piperidino, morpholino or homopiperidino.

The organic material is preferably a polymer processed at elevated temperatures. Particularly preferred organic polymers are the polyolefins, especially polypropylene and polyethylene, and polyamides. Most particularly the organic polymer is polypropylene.

The compounds of this invention are more effective processing stabilizers for polyolefins than the prior an compounds both in preventing molecular weight changes as well as preventing discoloration.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, mines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

31. Polysiloxanes such as the soft, hydrophilic polysiloxanes described, for example, in U.S. Pat. No. 4,259,467; and the hard polyorganosiloxanes described, for example, in U.S. Pat. No. 4,355,147.

32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

33. Radiation curable compositions containing ethylenically unsaturated monomers or oligomers and a polyunsaturated aliphatic oligomer.

34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |
| triethanolamine | triisopropanolamine |

1.9. Amides of β-(3,5-di-tert-butryl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example, diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1.2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-,5-chloro-3',5'-di-tert-butyl-, 5-chloro-3'-tert-butyl-5'-methyl-, 3'-sec-butyl-5'-tert-butyl-,4'-octoxy, 3',5'-di-tert-amyl-,3',5'-bis-(α,α-dimethylbenzyl),3'-tert-butyl-5'-(2-(omega-hydroxy-octa-(ethyleneoxy)carbonylethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl)sebacate, bis-(1,2,2,6,6-pentamethylpiperidyl)sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4 -hydroxypiperidine and succinic acid, condensation product of N,N'-(2,2,6,6-tetra-methylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl)sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4 -octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]6-(4-chlorophenyl)-s-triazine; 2,4-bis[2-hydroxy-4-(2-hydroxy-4-(2 -hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4,6-tri-tert-butylphenyl)-pentaerythritol diphosphite, di-(2,4-di-tert-butyl-6 -methylphenyl)-pentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyldithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alphaheptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. Nos. 4,325,863, 4,338,244 or 5,175,312, or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)-benzofuran-2-one, 3-(4-acetoxy-3,5-dimethylphenyl)-5,7-di-tert-butyl-benzofuran-2-one, 3-(3,5-di-methyl-4-pivaloyloxyphenyl)-5,7-di-tert-butyl-benzofuran-2-one.

The co-stabilizers, with the exception of the benzofuranones listed under 11, are added for example in concentrations of 0.01 to 10%, relative to the total weight of the material to be stabilized.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. Nos. 4,325,863, 4,338,244 or 5,175,312.

Examples of such benzofuran-2-ones are compounds of the formula

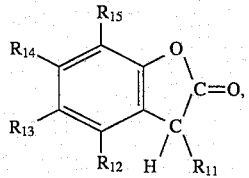

in which $R_{11}$ is phenyl or phenyl which is substituted by 1 to 3 alkyl radicals together having at most carbon atoms, alkoxy having 1 to 12 carbon atoms, alkoxycarbonyl having 2 to 18 carbon atoms or chlorine;

$R_{12}$ is hydrogen;

$R_{14}$ is hydrogen, alkyl having 1 to 12 carbon atoms, cyclopentyl, cyclohexyl or chlorine;

$R_{13}$ has the meaning of $R_{12}$ or $R_{14}$ or is a radical of the formula

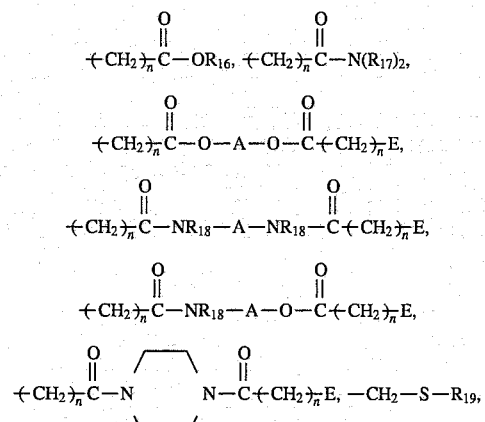

-continued $$-CH(C_6H_5)_n-\overset{O}{\underset{\|}{C}}-OR_{16} \text{ or } -D-E,$$

in which $R_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals together having at most 18 carbon atoms;

n is 0, 1 or 2;

the substituents $R_{17}$, independently of one another, are hydrogen, alkyl having 1 to 18 carbon atoms, cyclopentyl, cyclohexyl, phenyl, phenyl which is substituted by 1 or 2 alkyl radicals together having at most 16 carbon atoms, a radical of the formula

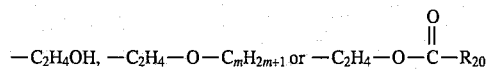

or together with the nitrogen atom to which they are attached form a piperidine or morpholine radical;

m is 1 to 18;

$R_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

$R_{18}$ is hydrogen, alkyl having 1 to 18 carbon atoms, cyclopentyl, cyclohexyl, phenyl, phenyl which is substituted by 1 or 2 alkyl radicals together having at most 16 carbon atoms, or is benzyl;

$R_{19}$ is alkyl having 1 to 18 carbon atoms;

D is —O—, —S—, —SO—, —SO$_2$—or —C(R$_{21}$)$_2$—;

the substituents $R_{21}$, independently of one another, are hydrogen, $C_1$-$C_{16}$alkyl, the two $R_{21}$ together containing 1 to 16 carbon atoms, $R_{21}$ is furthermore phenyl or a radical of the formula

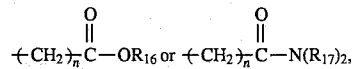

in which n, $R_{16}$ and $R_{17}$ are as defined above;

E is a radical of the formula

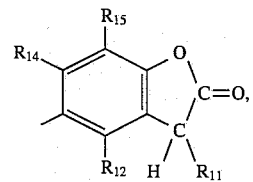

in which $R_{11}$, $R_{12}$ and $R_{14}$ are as defined above; and $R_{15}$ is hydrogen, alkyl having 1 to 20 carbon atoms, cyclopentyl, cyclohexyl, chlorine or a radical of the formula

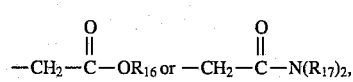

in which $R_{16}$ and $R_{17}$ are as defined above, or $R_{15}$ together with $R_{14}$ forms a tetramethylene radical.

Preference is given to those benzofuran-2-ones in which $R_3$ is hydrogen, alkyl having 1 to 12 carbon atoms, cyclopentyl, cyclohexyl, chlorine or a radical of the formula

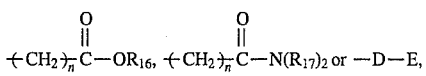

in which n, $R_{16}$, $R_{17}$, D and E are as defined above, $R_{16}$ is in particular hydrogen, alkyl having 1 to 18 carbon atoms, cyclopentyl or cyclohexyl.

Preference is given furthermore to those benzofuran-2-ones in which $R_{11}$ is phenyl or phenyl which is substituted by 1 or 2 alkyl radicals together having at most 12 carbon atoms; $R_{12}$ is hydrogen; $R_{14}$ is hydrogen or alkyl having 1 to 12 carbon atoms; $R_{13}$ is hydrogen, alkyl having 1 to 12 carbon atoms,

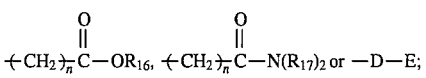

$R_{15}$ is hydrogen, alkyl having 1 to 20 carbon atoms,

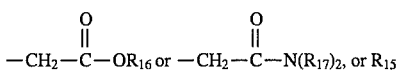

together with $R_{14}$ forms a tetramethylene radical, n, $R_{16}$, $R_{17}$, D and E being as defined at the beginning.

Of particular interest are also those benzofuran-2-ones in which $R_{11}$ is phenyl; $R_{13}$ is hydrogen, alkyl having 1 to 12 carbon atoms or —D—E; $R_{12}$ and $R_{14}$, independently of one another, are hydrogen or alkyl having 1 to 4 carbon atoms; and $R_{15}$ is alkyl having 1 to 20 carbon atoms, D and E being as defined at the beginning.

Of special interest are finally also those benzofuran-2-ones in which $R_{11}$ is phenyl; $R_{13}$ is alkyl having 1 to 4 carbon atoms or —D—E; $R_{12}$ and $R_{14}$ are hydrogen; and $R_{15}$ is alkyl having 1 to 4 carbon atoms, cyclopentyl or cyclohexyl, D being a group —$C(R_{21})_2$— and E being a radical of the formula

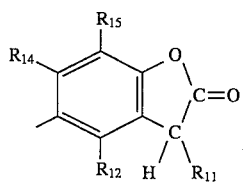

the substituents $R_{21}$ being identical to or different from one another and each being alkyl having 1 to 4 carbon atoms, and $R_{11}$, $R_{12}$, $R_{14}$ and R15 being as defined.

The amount of additional additives, in particular stabilizers, for example of the benzofuran-2-ones mentioned, can vary within wide limits. For example, 0.0005 to 10, preferably 0.001 to 5, in particular 0.01 to 2, % by weight thereof can be present in the compositions according to the invention.

Incorporation of the instant compound of formula I and, if desired, further additives in the polymer organic material is carded out by known methods, for example before or during moulding or by applying the dissolved or dispersed compounds to the polymer organic material, if appropriate with subsequent slow evaporation of the solvent. The beta, triclinic modification according to the invention can also be added to the materials to be stabilized in the form of a masterbatch containing them, for example, in a concentration of 2.5 to 25% by weight.

The instant compound of formula I according to the invention can also be added before or during polymerization or before crosslinking.

The instant compound of formula I according to the invention can be incorporated in the material to be stabilized in pure form or encapsulated in waxes, oils or polymers.

The instant compound of formula I according to the invention can also be sprayed onto the polymer to be stabilized. They are capable of diluting other additives (for example the above-mentioned customary additives) or their melts, thus enabling them to be sprayed onto the polymer to be stabilized also together with these additives. Addition by spraying during deactivation of the polymerization catalysts is particularly advantageous, it being possible, for example, for the steam used for deactivation to be used for spraying.

In the case of bead polymerized polyolefins, it may be advantageous, for example, to apply the instant compound of formula I according to the invention, if desired together with other additives, by spraying.

The materials thus stabilized can be used in a wide range of forms, for example as films, fibres, tapes, moulding compositions, profiles or as binders for paints, adhesives or cements.

As already mentioned, the organic materials to be protected are preferably organic, in particular synthetic, polymers. Of these, the materials being protected are particularly advantageously thermoplastic materials, in particular polyolefins. The excellent efficiency of the alkanolamine esters of acyclic phosphites of formula I as processing stabilizers (thermal stabilizers) should be mentioned in particular. To this end, it is advantageously added to the polymer before or during its processing. It is however also possible to stabilize other polymers (for example elastomers) or lubricants or hydraulic fluids against degradation, for example light-induced or thermal-oxidative degradation. For elastomers, see the above list of possible organic materials.

Suitable lubricants and hydraulic fluids are based, for example, on mineral or synthetic oils or mixtures thereof. Lubricants are known to one skilled in the art and described in the relevant technical literature, for example in Dieter Klamann, "Schmierstoffe und verwandte Produkte" (Verlag Chemic, Weinheim 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie" vol. 13, pages 85–94 (Verlag Chemic, Weinheim, 1977).

Accordingly, a preferred embodiment of the present invention is the process of using the instant compound of formula I for stabilizing organic materials against oxidative, thermal or light-induced degradation.

The instant compound according to the invention is preferably used as processing stabilizer (thermal stabilizer) of thermoplastic polymers.

The present invention also provides a process for stabilizing an organic material against oxidative, thermal or light-induced degradation, which comprises incorporating therein or applying thereto an instant compound of formula I.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl- 4-hydroxyhydrocinnamate), 1,3,5-trimethyl-2,4,6-tris(3,5-di-tert-butyl-4-hydroxybenzyl)benzene, 3,6-dioxaoctamethylene bis(3- methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5 -di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic and oxidant is neopentanetetrayl tetrakis(3,5-di-tert-butyl-4hydroxyhydrocinnamate), n-octadecyl 3,5-di-tert-butyl-4-hydroxyhydrocinnamate, 1,3,5-tri- methyl-2,4,6-tris(3,5-di-tert-butyl-4-hydroxybenzyl)benzene, 1,3,5-tris(3,5-di-tert-butyl-4hydroxybenzyl) isocyanurate, 2,6-di-tert-butyl-p-cresol or 2,2'-ethylidene-bis(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidine-4-yl)sebacate, di(1,2,2,6,6-pentamethylpiperidin-4-yl) (3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza- 21-oxodispiro[5.1.11.2]heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidinyl-4-yl/β,β,β',β'-tetramethyl-3,9-(2,4,8,10-tetraoxaspio[5.5]undecane) diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]- undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), and bis(1-octyloxy-2,2,6,6-tetramethylpiperidin-4-yl)sebacate.

A most preferred hindered amine compound is bis(2,2,6,6-tetramethylpiperidin-4-yl)sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis(amino-2,2,6,6-tetramethylpiperidine), N,N',N'',N'''-tetrakis[(4,6-bis(butyl-(2,2,6,6-tetramethyl-piperidin-4-yl)amino)-s-triazine-2-yl]1,10-diamino-4,7-diazadecane or bis(1-octyloxy-2,2,6,6-tetramethylpiperidin-4-yl)sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent brightstocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$-OCC-alkylene-COO$G_2$ wherein "alkylene" denotes an alkylene residue having from 2 to 14 carbon atoms and $G_1$ and $G_2$ are the same or different and each is an alkyl group having from 6 to 18 carbon atoms. Tri-esters which are of use as lubricating oil base stocks are those derived from trimethylolpropane and $C_6$-$C_{18}$ monocarboxylic acids or mixtures thereof, whereas suitable tetra-esters include those derived from pentaerythritol and a $C_6$-$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants

1. Alkylated Monophenols 2,6-Di-tert-butyl-4-methylphenol, 2,6-di-tert-butylphenol, 2-tert-butyl-4,6-dimethylphenol,2,6-di-tert-butyl-4-ethyl-phenol, 2,6-di-tert-butyl-4-n-butylphenol, 2,6-di-tert-butyl-4-i-butylphenol, 2,6-dicyclopentyl-4-methylphenol, 2-(β-methylcyclohexyl)-4,6-dimethylphenol, 2,6-di-octa-decyl-4-methylphenol, 2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5 '-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols 4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide.

9. Amides of β-(3,5-Di-tert-butyl;47hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants:

N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine, tert-octylated phenothiazine, 3,7-di-tert-octylphenothiazine.

Examples for other antioxidants:

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

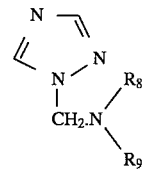

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an mine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and mines, 4-nonyl-phenoxy-acetic acid.

b) Nitrogen-containing compounds, e.g.

I. Primary, secondary or tertiary aliphatic or cycloaliphatic mines and mine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonyl-naphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an mine $Y-NH_2$ with an acid $R_{10}CO_2H$, as disclosed in DE-OS 3437 876 (German Offenlegungsschrift).

g) Compounds having the formula $$R_{12}-X_2-CH_2-CH(OH)-CH_2NR_{13}R_{14}$$

in which $X_2$ is —O—, —S—, —$SO_2$ —C(O)—O— or —N(Rd) in which $R_{12}$ is H or $C_1$–$C_{12}$alkyl, $R_{13}$ is unsubstituted $C_1$–$C_4$alkyl or $C_2$–$C_5$alkyl substituted by one to three hydroxyl groups, $R_{14}$ is hydrogen, unsubstituted $C_1$–$C_4$alkyl or $C_2$–$C_5$alkyl substituted by one to three hydroxyl groups provided that at least one of $R_{13}$ and $R_{14}$ is hydroxy-substituted, and $R_{12}$ is $C_2$–$C_{20}$alkyl —$CH_2$—CH(OH)—$CH_2NR_{13}R_{14}$ or $R_{12}$ is $C_2$–$C_{18}$alkenyl, $C_2$–$C_3$alkynyl or $C_5$–$C_{12}$cycloalkyl provided that, when $X_2$ is —O— or —C(O)—O—, $R_{12}$ is branched $C_4$–$C_{20}$alkyl. These compounds are described in GB Patent Specification 2172284A.

h) Compounds having the formula:

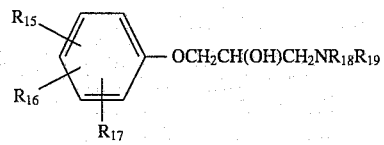

in which $R_{15}$, $R_{16}$, $R_{17}$ are, independently, hydrogen, $C_1$–$C_{15}$alkyl, $C_5$–$C_{12}$cycloalkyl, $C_6$–$C_{15}$aryl or $C_7$–$C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are:

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are:

Polymethacrylates, alkylated naphthalene derivatives.

Examples of dispersants/detergents are:

Polybutenylsuccinic acid-amides or-imides, polybutenylphosphonic acid derivatives, basic magnesium-, calcium-, and bariumsulfonates and -phenolates.

Examples of anti-wear additives and extreme pressure additives are:

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are for the purpose illustration only and are not to be construed to limit the scope of the instant invention in any manner whatsoever.

EXAMPLE 1

2,2',2"-Nitrilo{triethyl-tris[bis(2,4-di-tert-butylphenyl)]phosphite}

Into a solution of 5.2 g (35 mmol) of triethanolamine and 14.6 mL (105 mmol) of triethylamine in 200 mL of toluene at ambient temperature is added a solution of 50 g (105 mmol) of bis(2,4-di-tert-butylphenoxy)-chlorophosphine in 200 mL of toluene. The progress of the reaction is monitored by $^{31}$P NMR and the reaction is considered complete when the resonance at 161 ppm completely disappears. After completion of the reaction, the product is isolated by first removing the triethylamine hydrochloride by filtration and then concentrating the filtrate in vacuo. The reaction residue is purified by chromatography and the title compound is isolated as an off-white solid foam which is ground to a powder with a melting range of 56° to 65° C.

Analysis: Calcd. for $C_{90}H_{138}NO_9P_3$: C, 73.5; H, 9.5; N, 0.95. Found: C, 73.3; H, 9.8; N, 1.0.

EXAMPLE 2

N-Methyl-2,2'-imino{diethyl-bis[di-(2,4-di-tert-butylphenyl)]phosphite}

When the procedure of Example 1 is repeated using N-methyldiethanolamine in place of triethanolamine, the title compound is obtained as an off-white glass which is ground to a powder.

Analysis: Calcd. for $C_{61}H_{95}NO_6P_2$: C, 73.2; H, 9.6; N, 1.4. Found: C, 73.1; H, 9.5; N, 1.3.

EXAMPLE 3

2,2',2"-Nitrilo{triethyl-tris[bis(2,4-di-tert-amylphenyl)]phosphite}

When the procedure of Example 1 is repeated using bis(2,4-di-tert-amylphenoxy)-chlorophosphine in place of bis(2,4-di-tert-butylphenoxy)-chlorophosphine, the title compound is obtained as a light yellow viscous oil.

Analysis: Calcd. for $C_{102}H_{162}NO_9P_3$: N, 0.85. Found: N, 0.76.

EXAMPLE 4

2,2',2"-Nitrilo{triethyl-tris[bis(2,4-di-tert-butyl-6-methylphenyl)]phosphite}

A solution of 1 g (90 mmol) of 2,4-di-tert-butyl-6-methylphenol, 6.8 g (49 mmol) of phosphorus trichloride and 0.87 g (2.7 mmol) of tetrabutylammonium bromide in 20 mL of toluene is heated at 100° C. for four hours with evolution of hydrogen chloride. An additional 20 mL of toluene is added to the reaction mixture and 20 mL of solvent is removed by distillation to remove any remaining phosphorus trichloride. Into the resultant yellow solution, cooled to 60° C., are added 50 mL of toluene and 7.5 mL (5.5 g, 54 mmol) of triethylamine; followed by 2.24 g (15 mmol) of triethanolamine in 4 mL of tetrahydrofuran. The reaction mixture is warmed to 70° C. and heated for an additional three hours at this temperature.

The reaction mixture is then cooled to ambient temperature and poured into ice water. The resultant mixture is then extracted with ethyl acetate, the organic layer dried over anhydrous sodium sulfate and concentrated in vacuo to obtain 23.3 g of solid residue. The product is purified by suspending in cold ethanol followed by filtration to obtain 19.4 g (83%) of the title compound as a white powder with a melting point of 65°–67° C.

Analysis: Calcd. for $C_{96}H_{150}NO_9P_3$: C, 74.1; H, 9.7; N, 0.9. Found: C, 73.9; H, 9.7; N, 0.9.

EXAMPLE 5

Di-(2,6-diisopropylphenyl)-[2-(N,N-dimethylamino)ethyl]Phosphite

The procedure of Example 1 is repeated using 10 g (24 mmol) of bis(2,6-diisopropylphenoxy)chlorophosphine, 2.1 g (24 mmol) of N,N-dimethylethanolamine and 3.3 mL (24 mmol) of triethylamine in 50 mL of toluene to give 12 g of a crude oil. Purification of the crude oil by flash chromatography (silica gel, 24% ethyl acetate/1% triethylamine/75% hexane) gives 5.1 g (38.6% yield)of a white solid melting at 48°–52° C.

$^{31}$P NMR (121.47 MHz)(Benzene-d$_6$)(ppm): 139.8 ppm

EXAMPLE 6

2,2',2"-Nitrilo{triethyl-tris[bis(2,64-isopropyl) phenyl)]phosphite}

The procedure of Example 1 is repeated using 15 g (36 mmol) of bis(2,6-diisopropylphenoxy)chlorophosphine, 1.8 (12 mmol) of triethanolamine and 5 mL (36 mmol) of triethylamine in 60 mL of toluene to give 20 g of an oil. Purification of 5 g of the crude oil by flash chromatography (silica gel, 2% ethyl acetate/hexane) gives 2 g (40% recovery yield) of a colorless gum. The product is identified by mass spectroscopy (CI): M+1 =1302.

$^{31}$P NMR (121.47 MHz)(Benzene-d$_6$)(ppm): 138.7 ppm

EXAMPLE 7

Di-(2,4,6-tri-tert-butylphenyl)-[2-(N,N-dimethylamino)ethyl]Phosphite

Into a suspension of 0.74 g (17 mmol) of 55% sodium hydride in 20 mL of n-octane is added dropwise a solution of 1.5 g (17 mmol) of N,N-dimethylethanolamine in 5 mL of n-octane. After 16 hours of stirring at ambient temperature, a solution of 10 g (17 mmol) of bis(2,4,6-tri-tert-butylphenoxy)chlorophosphine and 10 mL of n-octane is added to the reaction mixture followed by heating to 100° C. for two hours. The reaction mixture is filtered and the filtrate is concentrated to 10 g of a crude solid. Flash chromatography (silica gel, 15% ethyl acetate/hexane) is used to purify the crude product to give 2 g (18% yield) of white crystals melting at 127°–132° C. The product is identified by mass spectroscopy (CI): M+1=642.

$^{31}$P NMR (121.47 MHz)(Benzene-d$_6$)(ppm): 156.2 ppm

EXAMPLE 8

2,2',2"-Nitrilo{triethyl-tris[di(2,4,6-tri-tert-butyl) phenyl)]phosphite}

The title compound is prepared by the procedure of Example 7 using bis(2,4,6-tri-tert-butylphenoxy)chlorophosphine and triethanolamine.

EXAMPLE 9

2,2',2"-Nitrilo{triethyl-tris[(2,4,6-tri-tert-butyl)phenyl)-(2,4-di-tert-butylphenyl)]phosphite}

The title compound is prepared by the procedure of Example 7 using (2,4,6-tri-tert-butylphenoxy)-(2,4 -di-tert-butylphenoxy)chlorophosphine and triethanolamine.

EXAMPLE 10

(2,4,6-Tri-tert-butylphenyl)-(2,4-di-tert-butylphenyl)-[2-(N,N-dimethylamino)ethyl]Phosphite The title compound is prepared by the procedure of Example 7 using (2,4,6-tri-tert-butylphenoxy)-(2,4 -di-tert-butylphenoxy)chlorophosphine and N,N-dimethylethanolamine.

EXAMPLE 11

Di-(2-tert-butyl-6-isopropylphenyl)-[2-(N,N-dimethylamino)ethyl]Phosphite

The title compound is prepared by the procedure of Example 7 using bis(2-tert-butyl-6-isopropylphenoxy)chlorophosphine and N,N-dimethylethanolamine.

EXAMPLE 12

2,2',2"-Nitrilo{triethyl-tris[di(2-tert-butyl-6-isopropylphenyl)]phosphite}

The title compound is prepared by the procedure of Example 7 using bis(2-tert-butyl-6-isopropylphenoxy)chlorophosphine and triethanolamine.

EXAMPLE 13

2,2',2"-Nitrilo{triethyl-tris[di(2,6-diethylphenyl)] phosphite}

The title compound is prepared by the procedure of Example 7 using bis(2,6-diethylphenoxy)chlorophosphine and triethanolamine.

EXAMPLE 14

Di-(2,6-diethylphenyl)-[2-(N,N-dimethylamino)ethyl]Phosphite

The title compound is prepared by the procedure of Example 7 using bis(2,6-diethylphenoxy)chlorophosphine and N,N-dimethylethanolamine.

EXAMPLE 15

Process Stabilization of Polypropylene at 525° F. (274° C.)

The base formulation comprises unstabilized, high yield/ high selectivity Spheripol polypropylene (PROFAX® 6501, Himont) containing 0.075% by weight of calcium stearate. The test additives are incorporated into the polyproylene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder (extruder screw to wall clearance adjusted tighter than normal for harsher than normal processing conditions) at 525° F. (274° C.) with a residence time of 90 seconds.

After each of the first and fifth extrusions, the melt flow rate (in grams/10 minutes) is determined by ASTM method D1238 on the pellets obtained from the extruder. The results are given in the table below.

| Additive | Concentration (% by weight) | Melt Flow after Extrusion | |
| --- | --- | --- | --- |
| | | 1 | 5 |
| None | — | 13.0 | 59.7 |
| Compound of Example 1 | 0.075 | 5.5 | 10.1 |

These results show that the stabilized composition of the instant invention provides greatly improved melt flow stabilization to polypropylene.

EXAMPLE 16

Process Stabilization of Polypropylene at 525° F. (274° C.)

Following the procedure of Example 15, polypropylene containing a phenolic antioxidant in combination with an instant compound is extruded and the melt flow rate (in grams/10 minutes) determined by ASTM method D1238 on the pellets obtained from the extruder after each of the first and fifth extrusions. The results are given in the table below.

| Additive* | Concent. (% by wt) | Melt Flow Values after Extrusion 1 | 5 |
|---|---|---|---|
| AO A | 0.075 | 8.9 | 19.3 |
| AO A plus Example 1 Compound | 0.075 0.075 | 4.7 | 6.8 |

*AO A is neopentanetetrayl tetrakis(3,5-di-tert-butyl-4-hydroxyhydrocinnamate).

The combination of a phenolic antioxidant plus an instant compound provides excellent melt flow stabilization; better stabilization than obtained by the use of a phenolic antioxidant alone.

EXAMPLE 17

Color Stabilization of Polypropylene

This example illustrates the color stabilizing effectiveness of the instant compounds in combination with a phenolic antioxidant in polypropylene.

Using the procedure described in Example 15, polypropylene containing a phenolic antioxidant in combination with an instant compound is extruded into pellets. Using the pellets obtained after each of the first and fifth extrusions as described in Example 5, the pellets are compression molded into 125 mil (3.2 mm) thick plaques at 193° C. Specimen yellowness index (YI) values are determinated according to ASTM method D1925. Lower YI values indicates less discoloration. The results are given in the table below.

| Additive* | Concentration (% by weight) | Yellowness YI after Extrusion 1 | 5 |
|---|---|---|---|
| AO A | 0.075 | 7.4 | 9.7 |
| AO A plus Example 1 Compound | 0.075 0.075 | 7.1 | 8.7 |

*AO A is neopentanetetrayl tetrakis(3,5-di-tert-butyl-4-hydroxyhydrocinnamate).

The stabilizer combination of a phenolic antioxidant and an instant compound provides more resistance to discoloration in the polypropylene than the use of a phenolic antioxidant alone.

What is claimed is:

1. A composition stabilized against thermal, oxidative and actinic induced degradation which comprises
   (a) a polyolefin, a lubricant, lubricating oil, natural fat or wax, or fat or wax based on a synthetic ester, subject to thermal, oxidative or actinic induced degradation, and
   (b) an effective stabilizing amount of an alkanolamine ester of formula I

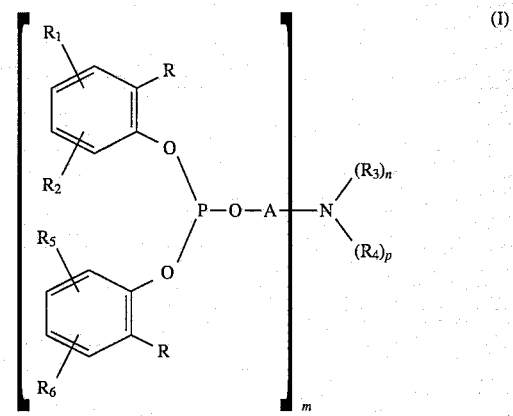

wherein m is 1–3, such that when:
   m is 1, then n is 1 and p is 1;
   m is 2, then n is 1 and p is 0;
   m is 3, then n is 0 and p is 0;
   A is alkylene of 2 to 8 carbon atoms or cycloalkylene of 5 to 6 carbon atoms;
   R is alkyl of 2 to 8 carbon atoms,
   $R_1$ and $R_5$ are alkyl of 1 to 8 carbon atoms, and $R_1$ $R_5$ are in the ortho or para position to the phosphite oxygen in each of the phenyl rings
   $R_2$ and $R_6$ are independently hydrogen or alkyl of 1 to 18 carbon atoms or phenyl;
   $R_3$ is hydrogen, alkyl of 1 to 18 carbon atoms, phenyl or a group of the formula

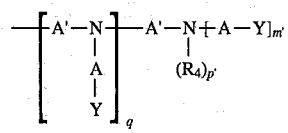

wherein Y is a group of the formula

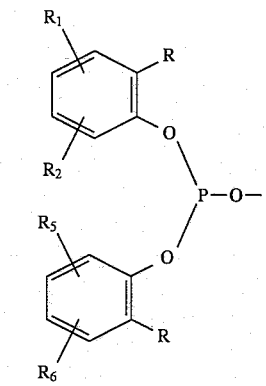

A' is alkylene of 2 to 8 carbon atoms or cycloalkylene of 5 to 6 carbon atoms,
m' is 1 or 2, when m' is 1, then p' is 1,
when m' is 2, then p' is 0, and
q is 0–5 with A, R, $R_1$, $R_2$, $R_5$ and $R_6$ being as previously defined, with the proviso that, when p and q are 0, then —N—A'—N— may be a diazacycloalkylene group of 4 to 10 carbon atoms; or when m is 1 and p is 0, then N—$R_3$ is an azacycloalkyl group of 4 to 10 carbon atoms or an azaoxacycloalkyl group of 4 to 7 carbon atoms; and $R_4$ is hydrogen, alkyl of 1 to 18 carbon atoms or phenyl; and with the further proviso that when R is tert-butyl, $R_1$ and $R_5$ are 4-tert-butyl, and $R_2$ $R_6$ are 6-methyl, then m is 3.

2. A composition according to claim 1 where in formula I of component (b), R is alkyl of 2 to 8 carbon atoms, $R_1$ and $R_5$ are alkyl of 1 to 8 carbon atoms, and $R_1$ and $R_5$ are in the ortho or para position to the phosphite oxygen in each of the phenyl rings.

3. A composition according to claim 1 where in formula I of component (b), m is 3, and n and p are 0.

4. A composition according to claim 1 where in formula I of component (b), R is iso-propyl, sec-butyl, tert-butyl, tert-amyl or tert-octyl group, $R_1$ and $R_5$ are alkyl of 1 to 8 carbons, and $R_1$ and $R_5$ are in the ortho or para position to the phosphite oxygen in each of the phenyl rings; and m is 3, and n and p are 0.

5. The composition according to claim 1 wherein component (b) is (a) 2,2',2"-nitrilo{triethyl-tris[bis(2,4-di-tert-butylphenyl)]phosphite};

(b) N-methyl-2,2'-imino{diethyl-bis[di-(2,4-di-tert-butylphenyl)]phosphite};

(c) 2,2',2"-nitrilo{triethyl-tris[bis(2,4-di-tert-amylphenyl)]phosphite};

(d) 2,2',2"-nitrilo{triethyl-tris[bis(2,4-di-tert-butyl-6-methylphenyl)]phosphite};

(e) di-(2,6-diisopropylphenyl)-[2-(N,N-dimethylamino)ethyl]phosphite;

(f) 2,2',2"-nitrilo{triethyl-tris[bis(2,6-diisopropyl)phenyl)]phosphite};

(g) di-(2,4,6-tri-tert-butylphenyl)-[2-(N,N-dimethylamino)ethyl]phosphite;

(h) 2,2',2"-nitrilo{triethyl-tris[di(2,4,6-tri-tert-butyl)phenyl)]phosphite};

(i) 2,2',2"-nitrilo{triethyl-tris[(2,4,6-tri-tert-butyl)phenyl)-(2,4-di-tert-butylphenyl)]phosphite};

(j) (2,4,6-tri-tert-butylphenyl)-(2,4-di-tert-butylphenyl)-[2-(N,N-dimethylamino)ethyl]phosphite;

(k) di-(2-tert-butyl-6-isopropylphenyl)-[2-(N,N-dimethylamino)ethyl]phosphite;

(l) 2,2',2"-nitrilo{triethyl-tris[di(2-tert-butyl-6-isopropylphenyl)]phosphite};

(m) 2,2',2"-nitrilo{triethyl-tris[di(2,6-diethylphenyl)]phosphite}; or (n) di-(2,6-diethylphenyl)-[2-(N,N-dimethylamino)ethyl]phosphite.

6. A composition according to claim 1 wherein the polyolefin is polyethylene or polypropylene.

7. A composition according to claim 6 wherein the polyolefin is polypropylene.

8. A composition according to claim 1 which additionally contains a phenolic antioxidant, a light stabilizer or a processing stabilizer.

9. A composition according to claim 1 which additionally contains as a coadditive at least one compound of the benzofuran-2-one type.

10. A process for stabilizing a polyolefin, a lubricant, lubricating oil, natural fat or wax, or fat or wax based on a synthetic ester against oxidative, thermal or actinic-induced degradation, which comprises incorporating therein or applying thereto the alkanolamine ester of formula I according to claim 1.

* * * * *